United States Patent [19]

Kolts et al.

[11] Patent Number: 5,077,446

[45] Date of Patent: Dec. 31, 1991

[54] METHANE CONVERSION

[75] Inventors: John H. Kolts, Ochelata, Okla.; Jack H. Lunsford, College Station, Tex.

[73] Assignee: Phillips Petroleum Company, Bartlesville, Okla.

[21] Appl. No.: 713,653

[22] Filed: Mar. 19, 1985

[51] Int. Cl.$^5$ .............................................. C07C 2/00
[52] U.S. Cl. .................. 585/500; 585/415; 585/417; 585/418; 585/654; 585/656; 585/657; 585/658; 585/661; 585/943
[58] Field of Search ............. 585/415, 417, 418, 500, 585/654, 656, 657, 658, 661, 943

[56] References Cited

U.S. PATENT DOCUMENTS

| | | | |
|---|---|---|---|
| 1,801,382 | 4/1931 | Uretzel | 585/943 |
| 1,863,212 | 6/1932 | Winkler | 585/415 |
| 1,987,092 | 1/1935 | Winkler | 585/417 |
| 2,123,799 | 7/1938 | Piabielniak | 585/417 |
| 2,396,697 | 3/1946 | Gorin | 585/415 |
| 2,467,551 | 4/1946 | Gorin | 585/943 |
| 4,237,658 | 12/1980 | Mitchell, III et al. | 585/417 |
| 4,497,970 | 2/1985 | Young | 585/415 |
| 4,513,164 | 4/1985 | Olah | 585/943 |
| 4,523,049 | 6/1985 | Jones et al. | 585/500 |
| 4,523,050 | 6/1985 | Jones et al. | 585/943 |

FOREIGN PATENT DOCUMENTS 3237079 4/1984 Fed. Rep. of Germany ...... 585/500

OTHER PUBLICATIONS

Symposium on the New Surface Science in Catalysis Presented before the Division of Colloid and Surface Chem. and the Division of Petroleum Chemistry, Inc., Philadelphia Meeting, Evidence for the Formation of Gas Phase Radicals at Surfaces, Aug. 1984.

Primary Examiner—Patrick P. Garvin
Assistant Examiner—E. D. Irzinski
Attorney, Agent, or Firm—K. K. Brandes

[57] ABSTRACT

A method for the oxidative conversion of methane, at a high conversion and high selectivity to ethylene and ethane, in which a methane-containing gas, such as a natural gas, and an oxygen-containing gas are contacted with a contact material comprising lithium, in an effective amount, preferably 0.1 to 50 wt. % (expressed as the metal), and magnesium oxide, as by passing a mixture of the methane-containing gas and the oxygen-containing gas through a body of the contact material.

27 Claims, No Drawings

METHANE CONVERSION

The present invention relates to methane conversion. In a more specific aspect, the present invention relates to methane conversion to higher hydrocarbons. In a still more specific aspect, the present invention relates to methane conversion to ethylene and ethane.

BACKGROUND OF THE INVENTION

Olefins, such as ethylene and propylene have become major feedstocks in the organic chemical and petrochemical industries. Of these, ethylene is by far the more important chemical feedstock, since the requirements for ethylene feedstocks are about double those for propylene feedstocks. Consequently, feedstocks for the production of ethylene are in relatively short supply.

Numerous suggestions have been made for the production of ethylene from various feedstocks by a variety of processes.

At the present time, ethylene is produced almost exclusively by dehydrogenation or pyrolysis of ethane and propane, naptha and, in some instances, gas oils. About 75% of the ethylene is produced by steam cracking of ethane and propane derived from natural gas. However, natural gas contains as little as 5 volume percent and, in rare instances, as much as 60 volume percent of hydrocarbons other than methane, the majority of which is ethane. However, typical natural gases contain less than about 12 to 15% of ethane. In addition to the relatively small quantities of ethane and propane available for use, separation of these components from natural gas is itself an expensive and complex process usually involving compression and expansion, cryogenic techniques and combinations thereof.

It would, therefore, be highly desirable to be able to produce ethylene from the much more abundant methane. However, methane's high molecular stability, compared to other aliphatics, makes its use in ethylene production difficult and no significant amount of ethylene is produced commercially from methane at the present time.

Pyrolytic or dehydrogenative conversion of methane or natural gas to higher hydrocarbons has been proposed. However, relatively severe conditions, particularly temperatures in excess of 1000° C., are required. In addition, such reactions are highly endothermic and thus energy intensive. In order to reduce the severity of the conditions, particularly temperature, numerous proposals to catalyze pyrolytic reactions have been made. Some of these processes do, in fact, reduce the required temperatures, but the conversion of methane and the selectivity to ethylene are still quite low.

Another promising approach is the oxidative conversion of methane or natural gas to higher hydrocarbons. However, these techniques are still in the developmental stage and experimentation is hampered by differences of opinion and lack of a complete understanding of the process. For example, most workers in the art refer to the process as "oxidative coupling". However, there is little agreement with regard to the function performed by the oxygen and how this function is performed. Accordingly, the terminology, "oxidative coupling", will be avoided herein and the present process, irrespective of the function of the oxygen or of the manner in which it performs its function, will be referred to as "oxidative conversion of methane". In such processes, it is conventional to contact the methane with solid materials. The nature of these contact materials, the function thereof and the manner in which such function is performed are also subject to diverse theories. For example, workers in the art refer to the function of the contact material as a purely physical phenomenon, in some cases as adsorption-desorption, either of atomic or molecular oxygen and either on the surface or occluded within the solid material, oxidation-reduction utilizing multivalent metals capable of oxidation-reduction, adsorption and desorption of the hydrocarbons on the solid materials, a free radical mechanism, etc. Consequently, the solid materials, utilized in the process, are referred to as "contact materials", "promoters", "activators" and "catalysts". Accordingly, in order to avoid functional categorization, the terms "solid contact material" or "solid contact materials" will be utilized in the present application.

Based on the prior art, oxidative conversion of methane results in the formation of a variety of products. The most readily produced products are carbon dioxide, carbon monoxide and/or water and methanol, formaldehyde and other oxygenated hydrocarbons in combination with one or more of carbon dioxide, carbon monoxide and water. Higher hydrocarbons, particularly ethylene and ethane are either not formed or are formed in such small quantities that commercially viable processes have not been developed to date. Along with poor selectivity to higher hydrocarbons, particularly ethylene and ethane and still more particularly to ethylene, such processes also result in low conversions of the methane feed.

It is clear from the above that the suitability of particular contact materials is unpredictable. In addition to being dependent upon the type of contact material, the conversion of methane and selectivity to particular products also depends upon the conditions and the manner in which the reaction is carried out, and there is also little basis for predicting what conditions or what mode of operation will result in high conversions and selectivity to particular products.

SUMMARY OF THE INVENTION

It is therefore, an object of the present invention to provide an improved method for the conversion of methane. Another and further object is to provide an improved method for the oxidative conversion of methane. Yet another object is to provide a method for the oxidative conversion of methane at improved conversion levels. Another and further object of the present invention is to provide a method for the oxidative conversion of methane wherein improved selectivity to higher hydrocarbons is attained. A further object of the present invention is to provide a method for the oxidative conversion of methane which results in improved conversion and selectivity to higher hydrocarbons. A still further object of the present invention is to provide a method for the oxidative conversion of methane which results in improved selectivity to ethylene and ethane. Yet another object of the present invention is to provide a method for the oxidative conversion of methane which results in improved conversion and selectivity to ethylene and ethane. Another object of the present invention is to provide a method for the oxidative conversion of methane which results in improved selectivity to ethylene. Another and further object of the present invention is to provide a method for the oxidative conversion of methane which results in improved conversion and selectivity to ethylene. A still further object of the present invention is to provide a method for the oxidative conversion of methane which can be carried out in a simple, continuous manner. A further object of the present invention is to provide a method for the oxidative conversion of methane which can be carried out utilizing inexpensive starting materials. Another object of the present invention is to provide a method for the oxidative conversion of methane which can be carried out under relatively mild conditions. A still further object of the present invention is to provide a method for the oxidative conversion of methane utilizing an improved contact material.

These and other objects and advantages of the present invention will be apparent from the following description.

In accordance with the present invention, it has been found that methane can be converted to higher hydrocarbons by contacting a methane-containing gas and an oxygen-containing gas, with a contact material comprising lithium, in an effective amount, and magnesium oxide under conditions sufficient to produce significant amounts of higher hydrocarbons.

DETAILED DESCRIPTION OF THE INVENTION

In accordance with previous theories of the function and operation of contact materials for the oxidative conversion of methane to higher hydrocarbons, and particularly ethylene and ethane, the reaction has been carried out in the absence of an oxygen-containing gas, with the oxygen being supplied by the contact material. As a result, the most utilized modes of operation have included treating the contact material with an oxygen-containing gas, such as oxygen or air, for a period of time sufficient to produce a reducible oxide of multivalent metal, contacting the reducible metal oxide with methane and, thereafter "regenerating" the catalyst with an oxygen-containing gas. Similarly, certain contact materials are contacted with an oxygen-containing gas to cause adsorption of oxygen on the contact material, methane is contacted with the contact material containing adsorbed oxygen and, thereafter, the contact material is again treated with an oxygen-containing gas. In both instances, the contact material after treatment with an oxygen-containing gas is purged with an inert gas, such as nitrogen, to remove excess oxygen which has not reacted with or been adsorbed on the contact material. Consequently, several techniques have been followed, including, carrying out the contact with methane and the contact with oxygen-containing gas in separate reaction chambers or sequentially passing oxygen-containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material in the presence of an oxygen-containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, to the extent that they are most often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The oxygen-containing gas may be any suitable oxygen-containing gas, such as oxygen, oxygen-enriched air or air. The method of the present application has been effectively carried out utilizing air as a source of oxygen.

When utilized in the present invention, the term "diluent gas" is meant to include any gaseous material present in the methane-containing gas, the oxygen-containing gas or in the form of an added gas which is essentially inert with respect to the oxidative conversion of methane and, thus, does not significantly decrease the conversion of methane and/or the selectivity to the production of higher hydrocarbons.

The volumetric ratio of methane to oxygen should be in excess of 1/1, preferably it is between 1/1 and about 30/1 and still more preferably between about 4/1 and about 15/1. It has been found that a ratio of methane to oxygen of at least 1/1 is necessary, in accordance with the present invention, in order to obtain maximum conversion of methane and high selectivity to higher hydrocarbons, particularly ethylene.

It has further been found, in accordance with the present invention, that oxidative conversion of methane to higher hydrocarbons can be substantially improved by contacting the mixture of methane and oxygen-containing gas with a contact material comprising lithium and magnesium oxide. The term "effective amount" is used herein to identify the quantity of lithium which, when present in the contact material, results in a significant increase in the conversion and/or the selectivity to higher hydrocarbons, particularly ethylene and ethane and more particularly to ethylene, compared with magnesium oxide alone. Accordingly, in accordance with the present invention, the lithium is present in the contact material in amounts of at least an effective amount of lithium up to about 100 wt. %. While lithium alone has been found to result in the conversion of methane and selectivity to ethylene and ethane, the conversion and selectivity are low and it has been found that excessive amounts of lithium will deteriorate ceramic reactors, such as quartz reactors, in a short period of time. Likewise, magnesium oxide alone has been found to be effective for the conversion of methane and the selective production of ethylene and ethane. The contact material usually contains about 0.1 to 50 wt. % lithium, more preferably, between 0.1 and 15 wt. % and still more preferably between 1 and 10 wt. %. Ideally, the lithium content is between about 2 wt. % and about 7 wt. %. These weight percentages are the weight percent of elemental lithium metal based on the total weight of the magnesium oxide plus the lithium compound. This designation of weight percent lithium or other elements, as indicated, is utilized throughout the present application.

Substantially any compound or compounds of lithium may be utilized in the contact material so long as none of such compounds are detrimental to the effectiveness of the oxidative conversion of methane to higher hydrocarbon. The lithium is usually in the form of lithium oxide or carbonate prior to initiation of the method. During the course of the reaction, the lithium is believed to be converted to lithium carbonate. Accordingly, any lithium compound capable of conversion to lithium oxide or carbonate in the presence of the reaction media and/or products, particularly carbon dioxide, may be utilized as the preferred lithium compound.

The contact materials can be prepared by any suitable method known in the art for the preparation of such mixtures in a solid form. Conventional methods include co-precipitation from an aqueous, an organic or combination solution-dispersions, impregnation, dry mixing, wet mixing or the like, alone or in various combinations. In general, any method can be used which provides contact materials containing the prescribed components in effective amounts. The contact material can be prepared by mixing the ingredients, for example, lithium carbonate and magnesium hydroxide, in a blender with enough water to form a thick slurry. The slurry can then be dried, usually at a temperature sufficient to volatilize the water or other carrier, such as about 220° F. to about 450° F., and/or, thereafter, calcined, for example at about 700° F. to 1200° F., for from 1 to 24 hours. In a specific case, the material was dried overnight at about 300° C. and thereafter calcined for four hours at 775° C. Drying and/or calcining is preferably in the presence of an oxygen-containing gas or other oxidizing agent.

The contact material can also be promoted by the addition of tin in the form of its oxide or chloride, usually in the same amount, expressed as weight percent metal, as the lithium.

In the method of the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from atmospheric pressure to 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 20 cubic centimeters per minute per cubic centimeter of contact material.

The total flow velocities of all gaseous materials, including diluents, through a fixed bed reactor may be at any rate effective for the oxidative conversion reaction. For example from 50 to 5000 GHSV and preferably from 20 to 1000 GHSV.

In addition to the high conversion of methane and high selectivity to ethylene and ethane attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

In runs 1 through 41, the contact material was loaded in a quartz reactor having a thermocouple well centered in the contact material bed. The reactor was brought up to temperature under nitrogen or air and thereafter methane and air (or oxygen) flow was begun. The gas inlet system included electronic flow measurement, a three-zone furnace for heating reactant gases and the contact material and a downstream analysis system. The reactor effluent was snap sampled at any desired time and analyzed for all paraffins and olefins between $C_1$ and $C_4$ and $N_2$, $O_2$, CO and $CO_2$ by gas chromatography. All contact materials are referred to in terms of weight percent of the designated element.

RUNS 1-8

In this series of Runs, the contact material was prepared by mixing $Li_2CO_3$ and $Mg(OH)_2$ in a blender with sufficient water to form a thick slurry. The material was calcined overnight at 300° C. and thereafter for four hours at 775° C. to produce a contact material containing 7% lithium. 21 cc of contact material (19 grams) was loaded in the reactor and constant flows of 70 cc/min of $CH_4$ and 80 cc/min of air were passed downwardly through the reactor. The purpose of this test was to determine the longevity of the contact material.

RUNS 9-13

This series of Runs was carried out with the same contact material and in the same manner except that the ratio of methane to air was varied.

RUNS 14-17

This series of Runs was carried out utilizing a contact material prepared in the same manner, as pointed out above, except that the material contained 3% lithium. 20 cc of this contact material (17.2 grams) was utilized and the conditions were maintained constant for a period sufficient to test the longevity of this particular catalytic material.

RUNS 18-24

This series of Runs utilized the same contact material, containing 3% lithium, and the conditions were maintained the same while varying the temperature.

RUN 25

This test was conducted utilizing a contact material containing 3% Sn/3%Li/MgO at conditions considered optimal for Li/MgO.

RUNS 26-28

This series of Runs was carried out with a 3% Li/MgO contact material in the absence of oxygen but at the other conditions found most effective for the lithium/magnesium oxide contact material.

RUNS 29-30

These Runs were also conducted under the same conditions found to be effective for the lithium/magnesium oxide contact material, but utilizing only magnesium oxide as a contact material.

RUNS 31-33

This series of tests was carried out utilizing essentially the same conditions found effective for the lithium/magnesium contact material but depositing 3% lithium on various known catalyst base materials.

RUNS 34-37

These Runs were also carried out under essentially the same conditions found effective for the lithium/magnesium oxide contact material but utilizing quartz as a contact material instead.

RUNS 38-41

These runs were conducted utilizing Pb and Pb/Li deposited on an $Al_2O_3$ carrier.

The variables and results of this series of tests are set forth in Table I below. Conversion is percent of methane converted. Selectivity and yields are based on mole percent of methane feed converted to a particular product. The $CH_4$ rate is expressed as cc/min/cc of contact material. The volumetric ratio of $CH_4$ to oxygen is also parenthetically given in terms of cc/min of $CH_4$ per cc/min of other gases (air or $N_2$), per cent.

TABLE I

| Run | Contact Material | Temp °C. | Vol $CH_4/O_2$ ($CH_4$/Air) | $CH_4$ Rate cc/min/cc | Time min. | Conv % | Selectivity % $C_2^=$ | $C_2$ | $C_2$'s | $C_3^=$ | $C_3$ | $CO_2$ | CO | Yield % $C_2$'s | HC's |
|---|---|---|---|---|---|---|---|---|---|---|---|---|---|---|---|
| 1 | 7% Li/MgO | 706 | 4.4/1 (70/80) | 3.5 | 5 | 23.7 | 37.5 | 24.1 | 61.6 | 3.7 | 1.3 | 33.4 | — | 14.6 | 15.78 |
| 2 | 7% Li/MgO | 700 | 4.4/1 (70/80) | 3.5 | 40 | 22.0 | 38.0 | 25.0 | 67.0 | 4.0 | — | 33 | 1 | 14.74 | 15.62 |
| 3 | 7% Li/MgO | 708 | 4.4/1 (70/80) | 3.5 | 121 | 21.7 | 40.1 | 26.4 | 66.5 | 4.0 | 1.7 | 27.8 | — | 14.43 | 15.67 |
| 4 | 7% Li/MgO | 710 | 4.4/1 (70/80) | 3.5 | 182 | 22.5 | 38.6 | 24.5 | 63.1 | 3.3 | 1.7 | 31.1 | — | 14.2 | 15.32 |
| 5 | 7% Li/MgO | 696 | 4.4/1 (70/80) | 3.5 | 240 | 22.5 | 35.7 | 24.8 | 60.5 | 3.3 | 1.4 | 34.1 | 1.8 | 13.61 | 14.67 |
| 6 | 7% Li/MgO | 703 | 4.4/1 (70/80) | 3.5 | 270 | 22.5 | 38.6 | 25.4 | 64.0 | 3.5 | 1.8 | 30.7 | — | 14.4 | 15.59 |
| 7 | 7% Li/MgO | 704 | 4.4/1 (70/80) | 3.5 | 330 | 22.0 | 36.9 | 25.8 | 62.7 | 3.5 | 1.4 | 30.4 | 1.8 | 13.79 | 14.87 |
| 8 | 7% Li/MgO | 706 | 4.4/1 (70/80) | 3.5 | 385 | 22.0 | 37.3 | 27.4 | 65.7 | 3.5 | 1.5 | 30.2 | — | 14.45 | 15.55 |
| 9 | 7% Li/MgO | 654 | 1.5/1 (35/115) | 3.5 | 5 | 17.7 | 24.9 | 31.1 | 56.0 | — | — | 43.9 | — | 9.91 | 9.91 |
| 10 | 7% Li/MgO | 652 | 1.8/1 (40/110) | 3.5 | 5 | 12.7 | 20.4 | 31.7 | 52.1 | — | — | 47.9 | — | 6.62 | 6.62 |
| 11 | 7% Li/MgO | 641 | 2.5/1 (50/100) | 3.5 | 5 | 10.5 | 24.6 | 37.8 | 62.4 | — | — | 37.6 | — | 6.55 | 6.55 |
| 12 | 7% Li/MgO | 643 | 3.3/1 (60/90) | 3.5 | 5 | 8.9 | 22.2 | 39.7 | 61.9 | — | — | 38.1 | — | 5.51 | 5.51 |
| 13 | 7% Li/MgO | 643 | 4.4/1 (70/80) | 3.5 | 5 | 8.7 | 24.6 | 42.3 | 66.9 | — | — | 29.4 | ~2 | 5.82 | 5.82 |
| 14 | 3% Li/MgO | 685 | 4.4/1 (70/80) | 3.5 | 5 | 20.4 | 47.3 | 39.1 | 86.4 | 4.8 | 2.8 | 6.1 | — | 17.63 | 19.18 |
| 15 | 3% Li/MgO | 692 | 4.4/1 (70/80) | 3.5 | 40 | 23.0 | 40.2 | 23.7 | 63.9 | 3.7 | 1.9 | 30.9 | — | 14.70 | 15.99 |
| 16 | 3% Li/MgO | 694 | 4.4/1 (70/80) | 3.5 | 70 | 23.0 | 39.3 | 23.3 | 62.6 | 4.1 | 1.5 | 31.7 | — | 14.4 | 15.69 |
| 17 | 3% Li/MgO | 696 | 4.4/1 (70/80) | 3.5 | 155 | 21.7 | 39.4 | 24.1 | 63.5 | — | — | 31.0 | — | 13.78 | 13.78 |
| 18 | 3% Li/MgO | 660 | 4.4/1 (70/80) | 3.5 | 5 | 17.3 | 40.9 | 34.1 | 75.0 | 3.5 | 1.9 | 19.5 | — | 12.98 | 13.91 |
| 19 | 3% Li/MgO | 694 | 4.4/1 (70/80) | 3.5 | 5 | 25.7 | 38.0 | 26.1 | 64.1 | 3.3 | — | 32.6 | — | 16.47 | 16.32 |
| 20 | 3% Li/MgO | 735 | 4.4/1 (70/80) | 3.5 | 5 | 25.7 | 40.0 | 21.4 | 61.4 | 4.7 | 1.4 | 31.6 | — | 15.78 | 17.35 |
| 21 | 3% Li/MgO | 744 | 4.4/1 (70/80) | 3.5 | 5 | 24.4 | 42.0 | 21.7 | 63.7 | 5.0 | 1.4 | 29.9 | — | 15.54 | 17.10 |
| 22 | 3% Li/MgO | 746 | 4.4/1 (70/80) | 3.5 | 5 | 25.2 | 43.4 | 22.2 | 65.6 | 5.0 | 1.3 | 28.1 | — | 16.53 | 18.12 |
| 23 | 3% Li/MgO | 773 | 4.4/1 (70/80) | 3.5 | 5 | 24.8 | 43.9 | 19.2 | 63.1 | 5.3 | 0.8 | 30.7 | — | 15.65 | 17.16 |
| 24 | 3% Li/MgO | 803 | 4.4/1 (70/80) | 3.5 | 5 | 25.8 | 42.6 | 14.3 | 56.9 | 5.3 | 0.9 | 33.7 | 3 | 14.68 | 16.28 |
| 25 | 3% Sn/3% Li MgO | 704 | 4.4/1 (70/80) | 3.5 | 40 | 23.0 | 35.0 | 27.0 | 62.0 | 4.0 | 2.0 | 31.0 | — | 14.26 | 15.64 |
| 26 | 4% Li/MgO | 701 | $CH_4/N_2$ 4.4/1 (70/80) | 3.5 | 5 | 0.28 | — | 63.83 | 63.83 | — | — | 36.17 | — | 1.79 | 1.79 |
| 27 | 3% LiMgO | 701 | $CH_4/N_2$ 4.4/1 (70/80) | 3.5 | 5 | 0.11 | — | — | — | — | — | 100 | — | 0 | 0 |

TABLE I-continued

| Run | Contact Material | Temp °C. | Vol CH$_4$/O$_2$ (CH$_4$/Air) | CH$_4$ Rate cc/min/cc | Time min. | Conv % | Selectivity % ||||||| Yield % ||
|---|---|---|---|---|---|---|---|---|---|---|---|---|---|---|---|
| | | | | | | | C$_2$= | C$_2$ | C$_2$'s | C$_3$= | C$_3$ | CO$_2$ | CO | C$_2$'s | HC's |
| 28 | 3% LiMgO | 700 | CH$_4$/N$_2$ 4.4/1 (70/80) | 3.5 | 5 | 0.05 | — | — | — | — | — | 99.99 | — | 0 | 0 |
| 29 | MgO | 700 | CH$_4$/Air 4.4/1 (70/80) | 3.5 | 6 | 14.5 | 8.5 | 10.1 | 18.6 | — | — | 51.3 | 30.1 | 2.7 | 2.7 |
| 30 | MgO | 705 | CH$_4$/Air 4.4/1 (70/80) | 3.5 | 60 | 15.7 | 6.8 | 8.9 | 15.8 | 0.1 | — | 54.7 | 29.4 | 2.48 | 2.49 |
| 31 | 3% Li/SiO$_2$ | 716 | CH$_4$/Air 4.4/1 (70/80) | 3.5 | 5 | 2.0 | 11.0 | — | 11.0 | — | — | 27 | 62 | 0.22 | 0.22 |
| 32 | 3% Li/Al$_2$O$_3$ | 700 | CH$_4$/Air 4.4/1 (70/80) | 3.5 | 5 | 15 | — | 3.0 | 3.0 | — | — | 64 | 33 | 0.45 | 0.45 |
| 33 | 3% Li/CaSiO$_3$ | 717 | CH$_4$/Air 4.4/1 (70/80) | 3.5 | 5 | 3.0 | — | — | — | — | — | 48 | 52 | 0 | 0 |
| 34 | Quartz | 671 | CH$_4$/Air 4.4/1 (70/80) | 3.5 | 5 | 0 | — | — | — | — | — | — | — | 0 | 0 |
| 35 | Quartz | 742 | CH$_4$/Air 4.4/1 (70/80) | 3.5 | 5 | 0 | — | — | — | — | — | — | — | 0 | 0 |
| 36 | Quartz | 803 | CH$_4$/Air 4.4/1 (70/80) | 3.5 | 5 | 1.6 | — | 40.02 | 40.02 | — | — | 60 | — | 0.64 | 0.64 |
| 37 | Quartz | 740 | CH$_4$/Air 4.4/1 (70/80) | 3.5 | 5 | 0 | — | — | — | — | — | — | — | 0 | 0 |
| 38 | 25% Pb/Al$_2$O$_3$ | 670 | CH$_4$/Air 4.4/1 (70/80) | 3.5 | 3 | 26.4 | 5.2 | 3.0 | 8.2 | — | — | 91.8 | — | 2.16 | 2.16 |
| 39 | 25% Pb/Al$_2$O$_3$ | 670 | CH$_4$/Air 4.4/1 (70/80) | 3.5 | 90 | 16.7 | 8.9 | 8.7 | 17.6 | — | — | 78.5 | 3.9 | 2.94 | 2.94 |
| 40 | 25% Pb/0.2% Li/Al$_2$O$_3$ | 705 | CH$_4$/Air 4.4/1 (70/80) | 3.5 | 3 | 21.0 | 6.7 | 1.8 | 8.5 | — | — | 91.5 | — | 1.79 | 1.79 |
| 41 | 25% Pb/0.2% Li/Al$_2$O$_3$ | 705 | CH$_4$/Air 4.4/1 (70/80) | 3.5 | 43 | 16.7 | 8.7 | 3.7 | 12.4 | — | — | 73.3 | 14.3 | 2.07 | 2.07 |

Another series of tests was carried out in a smaller reactor in which 4 grams of 3 wt % Li/MgO was utilized. This contact material was dried by treating with oxygen at 465° C. for one hour. Oxygen was used instead of air and helium was substituted for the nitrogen in the air as a diluent in the reactor. The reactor was also a quartz reactor operated in a down flow manner and had a thermocouple well in the middle of the catalyst bed. Methane, oxygen and helium were passed through individual flow meters and combined for passage through the reactor. Effluent gases were analyzed in a gas chromatograph for ethylene, ethane, carbon dioxide and carbon monoxide. In addition to showing the effects of varying the temperature and the ratio of methane to oxygen, this series of runs also, to some extent, indicates the effects of varying the methane flow rate. The times given in the Table are times for a "preliminary" reaction or the time believed optimum to reach a steady state. Effluent was analyzed continuously and the results given are typical during a period of about one hour following the "preliminary" reaction. The CH$_4$ rate is expressed as cc/min./g of contact material. Lithium is given as the wt. % of the elemental metal. The volumetric ratio of CH$_4$/O$_2$ is parenthetically stated as cc/min of CH$_4$ per cc/min of O$_2$.

TABLE II

| Run | Contact Material | Temp °C. | Vol CH$_4$/O$_2$ (CH$_4$/O$_2$) | CH$_4$ Rate cc/min/g | Time min. | Conv % | Selectivity % |||||| Yield % C$_2$'s |
|---|---|---|---|---|---|---|---|---|---|---|---|---|
| | | | | | | | C$_2$= | C$_2$ | C$_2$'s | CO$_2$ | CO | |
| 42 | 3% Li/MgO | 620 | 1/1 (4.5/4.5) | 1.13 | 65 | 6.44 | 12.24 | 29.94 | 42.18 | 52.35 | 5.46 | 2.71 |
| 43 | 3% Li/MgO | 620 | 1.8.1 (18/10) | 4.5 | 65 | 3.94 | 8.26 | 26.36 | 34.62 | 59.57 | 5.82 | 1.36 |
| 44 | 3% Li/MgO | 620 | 2/1 (3/1.5) | 0.75 | 60 | 6.82 | 18.06 | 43.61 | 61.67 | 38.33 | 0 | 4.21 |
| 45 | 3% Li/MgO | 620 | 3/1 (4.5/1.5) | 1.13 | 85 | 5.45 | 17.98 | 48.99 | 66.97 | 33.03 | 0 | 3.65 |
| 46 | 3% Li/MgO | 620 | 4.5/1 (4.5/1) | 1.13 | 60 | 20 | 25.5 | 26.1 | 51.6 | 42.9 | 5.6 | 10.32 |
| 47 | 3% Li/MgO | 620 | 9/1 (18/2) | 4.5 | 60 | 10.48 | 23.4 | 33.6 | 57.0 | 37.5 | 5.4 | 5.97 |
| 48 | 3% Li/MgO | 620 | 18/1 | 4.5 | 60 | 7.65 | 23.4 | 40.7 | 64.1 | 31.3 | 4.5 | 4.90 |

TABLE II-continued

| Run | Contact Material | Temp °C. | Vol CH$_4$/O$_2$ (CH$_4$/O$_2$) | CH$_4$ Rate cc/min/g | Time min. | Conv % | Selectivity % C$_2$= | C$_2$ | C$_2$'s | CO$_2$ | CO | Yield % C$_2$'s |
|---|---|---|---|---|---|---|---|---|---|---|---|---|
| 49 | 3% Li/MgO | 620 | 18/1 (18/1) | 4.5 | 180 | 6.23 | 18.6 | 39.3 | 57.9 | 36.1 | 6.0 | 3.61 |
| 50 | 3% Li/MgO* | 620 | 18/1 (18/1) | 4.5 | 180 | 4.66 | 23.06 | 54.43 | 77.49 | 22.51 | 0.0 | 3.61 |
| 51 | 3% Li/MgO | 670 | 1/1 (4.5/4.5) | 1.13 | 55 | 24.68 | 25.70 | 22.27 | 47.97 | 48.84 | 3.19 | 11.83 |
| 52 | 3% Li/MgO | 670 | 1.8/1 (18/10) | 4.5 | 170 | 21.25 | 25.76 | 20.91 | 46.67 | 49.46 | 3.87 | 9.91 |
| 53 | 3% Li/MgO | 670 | 2/1 (3/1.5) | 0.75 | 60 | 20.71 | 30.84 | 30.93 | 61.77 | 36.61 | 1.62 | 12.79 |
| 54 | 3% Li/MgO | 670 | 3/1 (4.5/1.5) | 1.13 | 100 | 18.16 | 32.32 | 33.47 | 66.29 | 32.45 | 1.26 | 12.04 |
| 55 | 3% Li/MgO | 670 | 3/1 (4.5/1.5) | 1.13 | 60 | 27.51 | 32.9 | 23.3 | 56.2 | 41.6 | 2.2 | 15.46 |
| 56 | 3% Li/MgO* | 670 | 3/1 (4.5/1.5) | 1.13 | 60 | 27.54 | 33.32 | 23.56 | 56.88 | 41.82 | 1.30 | 15.66 |
| 57 | 3% Li/MgO | 670 | 3.96/1 (22.2/5.6) | 5.55 | 60 | 21.12 | 32.9 | 24.4 | 57.3 | 40.0 | 2.7 | 12.10 |
| 58 | 3% Li/MgO | 670 | 4.5/1 (4.5/1) | 1.13 | 120 | 19.17 | 35.6 | 30.2 | 65.8 | 32.7 | 1.4 | 12.61 |
| 59 | 3% Li/MgO | 720 | 1/1 (4.5/4.5) | 1.13 | 60 | 51.42 | 24.12 | 11.39 | 35.51 | 62.14 | 2.36 | 18.25 |
| 60 | 3% Li/MgO | 720 | 1.8/1 (18/10) | 4.5 | 130 | 38.16 | 29.10 | 13.92 | 43.02 | 54.17 | 2.81 | 16.42 |
| 61 | 3% Li/MgO | 720 | 2/1 (3/1.5) | 0.75 | 60 | 37.04 | 30.77 | 19.01 | 49.78 | 49.19 | 1.03 | 18.43 |
| 62 | 3% Li/MgO | 720 | 3/1 (4.5/1.5) | 1.13 | 90 | 25.56 | 35.76 | 26.07 | 61.83 | 38.17 | 0 | 15.80 |
| 63 | 3% Li/MgO | 770 | 1/1 (4.5/4.5) | 1.13 | 60 | 58.82 | 20.97 | 8.18 | 29.15 | 69.95 | 0.82 | 17.15 |
| 64 | 3% Li/MgO | 770 | 1/1 (18/18) | 4.5 | 70 | 57.80 | 20.90 | 5.73 | 26.63 | 70.90 | 2.44 | 15.39 |
| 65 | 3% Li/MgO | 770 | 1.8/1 (18/10) | 4.5 | 60 | 39.69 | 29.50 | 10.62 | 40.12 | 58.11 | 1.74 | 15.93 |
| 66 | 3% Li/MgO | 770 | 3/1 (4.5/1.5) | 1.13 | 60 | 30.27 | 31.62 | 18.60 | 50.22 | 49.78 | 0.00 | 15.20 |
| 67 | 3% Li/MgO | 770 | 3/1 (18/6) | 4.5 | 70 | 58.82 | 35.72 | 17.06 | 52.78 | 45.67 | 1.52 | 14.01 |

*Left in reactor for about 1 month following a previous run.

While specific materials, conditions of operation, modes of operation and equipment have been referred to herein, it is to be recognized that these and other specific recitals are for illustrative purposes and to set forth the best mode only and are not to be considered limiting.

What is claimed is:

1. A method for the conversion of methane comprising:
    contacting a methane-containing gas and an oxygen-containing gas with a solid contact material selected from the group consisting of:
    (1) a contact material, consisting essentially of: (a) a material selected from the group consisting of lithium and compounds containing lithium, in an effective amount, and, (b) magnesium oxide; and
    (2) a contact material, consisting essentially of: (a) a material selected from the group consisting of lithium and compounds containing lithium, in an effective amount, (b) a material selected from the group consisting of chloride ions and compounds containing chloride ions, and (c) magnesium oxide,
    under conditions sufficient to produce significant amounts of higher hydrocarbons.

2. A method in accordance with claim 1 wherein the methane-containing gas is a natural gas.

3. A method in accordance with claim 1 wherein the oxygen-containing gas is air.

4. A method in accordance with claim 1 wherein the oxygen-containing gas is oxygen.

5. A method in accordance with claim 1 wherein a diluent gas is present.

6. A method in accordance with claim 1 wherein the volumetric ratio of methane to oxygen is at least about 1/1.

7. A method in accordance with claim 1 wherein the volumetric ratio of methane to oxygen is between about 1/1 and 30/1.

8. A method in accordance with claim 1 wherein the lithium in the contact material is in the form of lithium oxide at the initiation of the method.

9. A method in accordance with claim 1 wherein the lithium in the contact material is in the form of lithium carbonate at the initiation of the method.

10. A method in accordance with claim 1 wherein the contact material is formed by heating a mixture of a lithium compound and magnesium hydroxide in the presence of an oxygen-containing gas.

11. A method in accordance with claim 1 wherein the contact material is formed by heating a mixture of lithium carbonate and a magnesium compound, which reacts with oxygen to produce magnesium oxide, in the presence of an oxygen-containing gas.

12. A method in accordance with claim 1 wherein the contact material is formed by heating a mixture lithium carbonate and magnesium hydroxide in the presence of an oxygen-containing gas.

13. A method in accordance with claim 1 wherein the temperature is maintained at at least 500° C.

14. A method in accordance with claim 1 wherein the temperature is maintained between about 500° C. and about 1500° C.

15. A method in accordance with claim 1 wherein the methane-containing gas and the oxygen-containing gas are simultaneously, continuously passed through a body of the contact material.

16. A method in accordance with claim 1 wherein the amount of lithium in the contact material is between about 0.1 wt. % and 50 wt. %, expressed in terms of the elemental metal based on the total weight of the contact material.

17. A method in accordance with claim 1 wherein at least one of the ratio of lithium to magnesium of the contact material, the ratio of methane to oxygen and the remaining conditions is selected to attain a high conversion of methane and a high selectivity to higher hydrocarbons.

18. A method in accordance with claim 17 wherein the ratio of methane to oxygen is selected to attain a high conversion of methane and a high selectivity to higher hydrocarbons.

19. A method in accordance with claim 17 wherein the temperature is selected to attain a high conversion of methane and a high selectivity to higher hydrocarbons.

20. A method in accordance with claim 17 wherein the high selectivity to higher hydrocarbons is a high selectivity to ethylene and ethane.

21. A method in accordance with claim 17 wherein the ratio of lithium to magnesium in the contact material is selected to attain a high conversion of methane and a high selectivity to higher hydrocarbons.

22. A method in accordance with claim 17 wherein the ratio of lithium to magnesium of the contact material, the ratio of methane to oxygen and the temperature are selected to attain a high conversion of methane and a high selectivity to higher hydrocarbons.

23. A method in accordance with claim 1 wherein at least one of the ratio of lithium to magnesium of the contact material, the ratio of methane to oxygen and the remaining conditions is selected to attain a high selectivity to ethylene and ethane.

24. A method in accordance with claim 23 wherein the ratio of methane to oxygen is selected to attain a high selectivity of ethylene and ethane.

25. A method in accordance with claim 23 wherein the temperature is selected to attain a high selectivity to ethylene and ethane.

26. A method in accordance with claim 23 wherein the ratio of lithium to magnesium of the contact material is selected to attain a high selectivity to ethylene and ethane.

27. A method in accordance with claim 23 wherein the ratio of lithium to magnesium of the contact material, the ratio of methane to oxygen and the temperature are selected to attain a high selectivity to ethylene and ethane.

* * * * *